United States Patent
Trabelsi et al.

[11] Patent Number: 5,843,787
[45] Date of Patent: Dec. 1, 1998

[54] METHOD ALLOWING THE FAST ASSESSMENT OF AT LEAST ONE PETROLEUM CHARACTERISTIC OF A ROCK SAMPLE-APPLICATION TO A RESERVOIR COMPRISING HEAVY OILS

[75] Inventors: Khomsi Trabelsi, Conflans Ste Honorine; Jean Espitalie, Le Vesinet, both of France

[73] Assignee: Institut Francais du Petrole, France

[21] Appl. No.: 714,441

[22] Filed: Sep. 16, 1996

Related U.S. Application Data

[63] Continuation of Ser. No. 498,059, Jul. 5, 1995, abandoned.

[30] Foreign Application Priority Data

Jul. 5, 1994 [FR] France .................................. 94 08383

[51] Int. Cl.$^6$ .................................................. G01N 31/12
[52] U.S. Cl. .............................. 436/139; 436/25; 436/28; 436/29; 436/30; 436/31; 436/32; 436/140; 436/141; 436/143; 436/145; 436/146; 436/150; 436/154; 436/155; 436/157
[58] Field of Search ................................ 436/25, 28, 29, 436/30, 31, 32, 139, 140, 141, 143, 149, 150, 154, 155, 157, 145, 146

[56] References Cited

U.S. PATENT DOCUMENTS

| | | | |
|---|---|---|---|
| 3,953,171 | 4/1976 | Espitalie et al. | 23/230 EP |
| 3,975,157 | 8/1976 | Smith . | |
| 4,153,415 | 5/1979 | Espitalie et al. | 23/230 EP |
| 4,213,763 | 7/1980 | Madec et al. | 23/230 EP |
| 4,229,181 | 10/1980 | Espitalie et al. | 23/230 EP |
| 4,248,599 | 2/1981 | Mommessin et al. . | |
| 4,352,673 | 10/1982 | Espitalie et al. . | |
| 4,519,983 | 5/1985 | Espitalie et al. | 422/78 |
| 4,629,702 | 12/1986 | Fan . | |
| 4,837,158 | 6/1989 | Thoulhoat et al. | 436/37 |
| 5,304,494 | 4/1994 | Eisenmann . | |

FOREIGN PATENT DOCUMENTS 0 026 012   4/1981   European Pat. Off. .

OTHER PUBLICATIONS

Philp "Application of pyrolysis–GS & Pyrolysis–GC–MS to fossil fuel research", Trends in Analytical Chemistry, vol. 1, No. 10, Jun. 1982.

"Application of pyrolysis—GC and pyrolysis GC–SM to fossil fuel research", R. Paul Philp, Trends in Analytical Chemistry, vol. 1(10), Jun. 1982).

*Primary Examiner*—Jill Warden
*Assistant Examiner*—S. Carrillo
*Attorney, Agent, or Firm*—Millen, White, Zelano & Branigan, P.C.

[57] ABSTRACT

A method allowing fast assessment of at least one petroleum characteristic of geologic sediments from a sample of these sediments, said method comprising heating the sample in a non-oxidizing atmosphere, and which method comprises different temperature rise stages; determining at least three magnitudes $S_{1r}$, $S_{2a}$ and $S_b$ representative of the quantity of hydrocarbons contained in said sample, and deducing at least one petroleum characteristic of the geologic sediment from these three magnitudes.

19 Claims, 5 Drawing Sheets

METHOD ALLOWING THE FAST ASSESSMENT OF AT LEAST ONE PETROLEUM CHARACTERISTIC OF A ROCK SAMPLE-APPLICATION TO A RESERVOIR COMPRISING HEAVY OILS

This is a continuation of the application Ser. No. 08/498,059 filed Jul. 5, 1995 now abandoned.

FIELD OF THE INVENTION

Background of the Invention

The present invention relates to a method for determining at least one petroleum characteristic of a sedimentary rock potentially or really producing hydrocarbons.

For a better understanding, it should be reminded that:

petroleum compounds, mainly the hydrocarbons extractable by organic solvents, form from the insoluble organic matter (kerogen) under the action of the temperature and pressure rise resulting from the burial of the sediments in a sedimentary basin, knowledge of the soluble organic matter (petroleum) on the one hand, and of the insoluble organic matter (kerogen) on the other hand, is of great interest in the field of oil exploration and development. In fact, it is well-known that:

the amount of petroleum formed in the sediments increases regularly with the depth of burial. It is therefore possible to assess the degree of evolution of the organic matter contained in these sediments and more particularly the interval of evolution corresponding to the main oil formation phase;

this petroleum will be ejected, under certain conditions, from the mother rock where it has formed to produce the petroleum accumulations in the reservoir rocks;

the nature of the insoluble organic matter contained in the rocks conditions the petroleum-generating potential of these rocks, i.e. their great ability to produce petroleum.

It appears then that the systematic analysis of these organic compounds allows to distinguish, among geologic sediments, those which afford the greatest interest for geologists:

sediments that have given rise to petroleum (mother rocks), sediments in which this petroleum has accumulated (reservoir rocks).

Knowledge of such information allows drillers to perform coring or reservoir test operations, which are long, costly and perilous operations, only advisedly, especially if these results can be acquired simultaneously with the drilling operations.

The ROCK-EVAL technique developed by the claimant and described notably in documents U.S. Pat. No. 3,953,171, U.S. Pat. No. 4,153,415, U.S. Pat. No. 4,229,181, U.S. Pat. No. 4,352,673 and U.S. Pat. No. 4,519,983 is well-known. This method, which is fast, practically automatic, can be suited to the characterization of rocks and of the hydrocarbons contained therein.

However, the existing ROCK-EVAL technique has been developed in order to characterize the mother rocks and does provide good information on the organic matter contained to mother rocks. This method is nevertheless not entirely satisfactory for characterizing the hydrocarbons contained in a reservoir rock, notably for identifying "tar-mat" deposits, as the heavy petroleum compounds (resins and asphaltenes) that settle at certain reservoir levels are commonly called. These tar-mats can present major drawbacks for production, notably by generating vertical permeability barriers or sometimes water inflows in productive horizons. The locating of these tar-mat levels and their lateral extension in the reservoir are therefore very important in order to understand, on the one hand, the processes of hydrocarbon accumulation and, on the other hand, to optimize the recovery of the hydrocarbons present.

The method according to the present invention is therefore an improvement of the ROCK-EVAL technique, allowing to characterize the different hydrocarbon sections, from the lightest to the heaviest, contained in a reservoir rock.

SUMMARY OF THE INVENTION

The present invention relates to an improved method allowing a fast assessment of at least one petroleum characteristic of a sample coming from geologic sediments, a method in which said sample is heated in a nonoxidizing atmosphere with several temperature rise stages. The method comprises the stages as follows:

a) the temperature of said sample is rapidly raised to a first temperature value below 200° C. for a predetermined time, b) from the first temperature value, the temperature of the sample is raised to a second temperature value according to a temperature gradient ranging between 1 and 12° C./minute, c) the temperature of the sample is raised from the second to a third temperature value at most equal to 800° C., preferably below 600° C., d) three magnitudes $S_{1r}$, $S_{2a}$ and $S_{2b}$ representative of the quantity of hydrocarbon-containing compounds contained in said sample are determined, e) at least one petroleum characteristic of said sample is deduced from these three magnitudes.

The magnitude $S_{1r}$ can be representative of the light hydrocarbons, such as those for which the carbon number is less than about 15, $S_{2a}$ can be representative of the heavier hydrocarbons, such as those for which the carbon number ranges between about 15 and 40, and $S_{2b}$ can be representative of the heavy hydrocarbon-containing compounds, such as those for which the carbon number is greater than about 40.

After raising the temperature to the third value, the residues of said sample can be burned and a fourth value $R_C$ representative of the quantity of residual organic carbon after pyrolysis can be determined.

The quantity Q of heavy products can be assessed according to the formula as follows:

$$Q = S_{2b} + 10 R_C / 0.9$$

Certain hydrocarbons of the sample can be distinguished by calculating a production index IP according to the formula as follows:

$$IP = (S_{1r} + S_{2a}) / (S_{1r} + S_{2a} + S_{2b})$$

and for a value $\mu$ ranging between 0 and 1, if $IP > \mu$, the sample can contain resins and/or asphaltenes and if $IP < \mu$, the sample can contain kerogen.

A value around 0.4 can be assumed for $\mu$.

In a variant of the method in which said sample is a piece of a reservoir rock:

a magnitude D can be calculated for several reservoir rock samples from at least one of the magnitudes $S_{1r}$, $S_{2a}$, $S_{2b}$ and Q, the API degree of the petroleum produced by said reservoir rocks of said samples can be measured, an approximate function $f$ relating the measured API degree to D can be determined, an approximate value of the API degree of the petroleum present in another reservoir rock can be determined by taking at least one sample of said other rock, by calculating the corresponding magnitude D and by using directly the function $f$.

According to another variant of the method in which said sample is a portion of the petroleum produced:

a magnitude D can be calculated for several samples coming from various reservoirs, from at least one of the magnitudes $S_{1r}$, $S_{2a}$, $S_{2b}$ and Q, the API degree of said samples can be measured, an approximate function $f1$ relating the measured API degree to D can be determined, an approximate value of the API degree of a petroleum of another origin can be determined by calculating the magnitude D corresponding to a sample of said petroleum of another origin and by using directly the function $f1$.

The magnitude D can be equal to $S_{2b}/(S_{1r}+S_{2a})$.
The magnitude D can be equal to $S_{1r}/(S_{1r}+S_{2a}+Q)$.
The magnitude D can be equal to $(S_{1r}+S_{2a})/(S_{1r}+S_{2a}+Q)$.
The function $f$ or $f1$ can be of the form as follows:

$$D = a \times 10^{b \times e^{-\alpha x}} + c$$

x being the API degree; a ranges between 0.11 and 0.12 and is preferably equal to 0.11482; b ranges between 1.7 and 2 and is preferably equal to 1.83; c is close to zero; α is close to 2.

BRIEF DESCRIPTION OF THE DRAWINGS

Other features and advantages of the invention will be clear from reading the description hereafter given by way of non limitative examples, with reference to the accompanying drawings in which.

DESCRIPTION OF THE PREFERRED EMBODIMENTS

Figure 1:
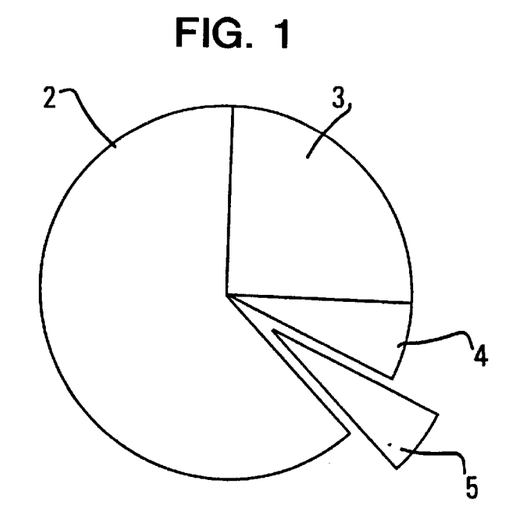
FIG. 1 diagrammatically shows the composition of an oil rock.

FIG. 1 diagrammatically illustrates the composition of a sedimentary rock sample, for example a piece of drill cuttings from a geologic formation crossed by a hole in the process of being drilled.

Zone 2 represents the quantity of mineral material, zone 3 represents the quantity of hydrocarbons referred to as light hydrocarbons. The carbon number of these hydrocarbons is generally less than 15.

Zone 4 represents the quantity of intermediate hydrocarbons between the light hydrocarbons and the heavy hydrocarbons. They can generally be classified between $C_{15}$ and $C_{40}$.

Zone 5 represents the quantity of heavy hydrocarbon-containing compounds, resins, asphaltenes and/or kerogen, generally greater than $C_{40}$.

The method according to the present invention allows to distinguish and to quantify the organic constituents contained in a rock sample, and particularly to differentiate the resins and the asphaltenes (NSO) from kerogen. During drilling through a producing or potentially producing geologic formation, samples of the formation can thus be taken according to the depth. These samples, once characterized by means of the present method, will allow to establish logs or imagings of the formation beds differentiated by the quantity and/or the nature of the hydrocarbons they contain.

The pyrolysis means and the means for oxidizing the pyrolysis residues will not be described here, it will be enough to refer to the documents cited above, which describe the means used for applying the present invention. It should however be reminded that the pyrolysis furnace co-operates with a device for detecting and for measuring the quantity of hydrocarbons in the pyrolyzed sample. The specific detection device (FIG. 5) includes for example a flame ionization type detector of conventional use in gas chromatography analyses. The detector delivers a signal S representative of the quantities of hydrocarbon-containing products measured. This signal can be transmitted to computing, storage and display means in which a specific software computes, displays and stores the different parameters representative of the characteristics of the hydrocarbons in presence.

The means described in documents U.S. Pat. No. 4,352, 673 and U.S. Pat. No. 4,519,983 can be used to measure the residual pyrolysis carbon. Automatic means can transfer pyrolysis residues into a specific oxidation furnace or, in a variant, a single furnace can be used for the pyrolysis in an inert atmosphere and for the oxidation.

Figure 2:
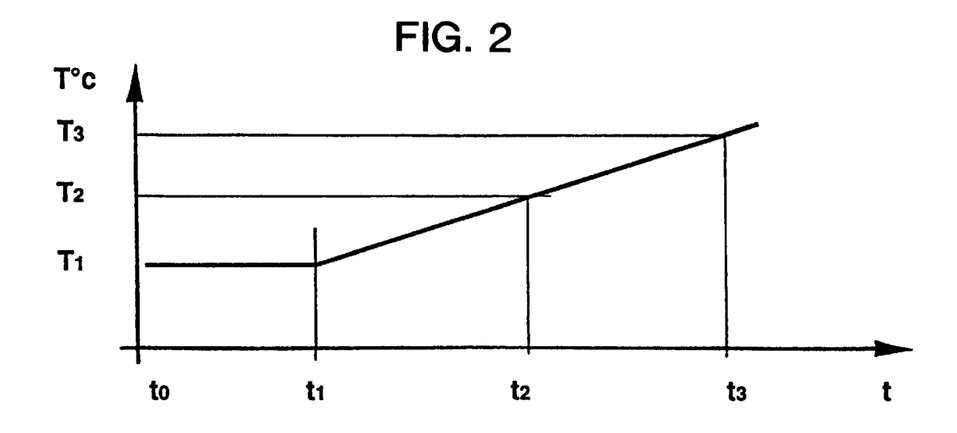
FIG. 2 shows the stages of heating of the sample as a function of time.

FIG. 2 represents the temperature sequences of the pyrolysis operation. At a time $t_0$, the sample is fed into an furnace heated to the initial temperature $T_1$. This initial temperature value is less than 200° C. and preferably close to 180° C. The duration $t_1-t_0$ of this first heating stage is for example about 15 minutes. From time $t_1$, a programmed pyrolysis stage starts, in which the temperature rise is imperatively less than 12° C./minute until the time $t_2$ corresponding to the temperature $T_2$. The value of this temperature is about 370° C., which substantially corresponds to the end of the thermovaporization stage of certain hydrocarbons and to the beginning of the stage of cracking by pyrolysis of the heavy compounds.

Preferably, the pyrolysis continues after the time $t_2$ so as to reach the temperature $T_3$, at most equal to 800° C. and preferably around 600° C. at the time $t_3$. The programmed temperature rise can be the same as that applied between the temperatures $T_1$ and $T_2$, i.e. less than 12° C./minute, which simplifies the method. However, in some cases, it will be possible to carry out the stage of cracking of the heavy hydrocarbons according to a temperature rise faster than 12° C./minute or different from the temperature gradient between $T_1$ and $T_2$.

Figure 3:
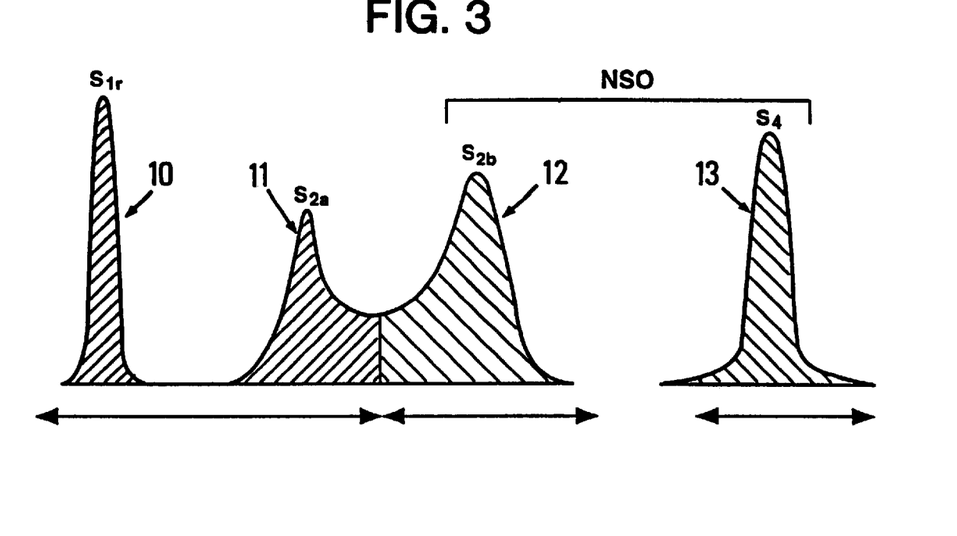
FIG. 3 shows the shape of signal S.
Figure 4A:
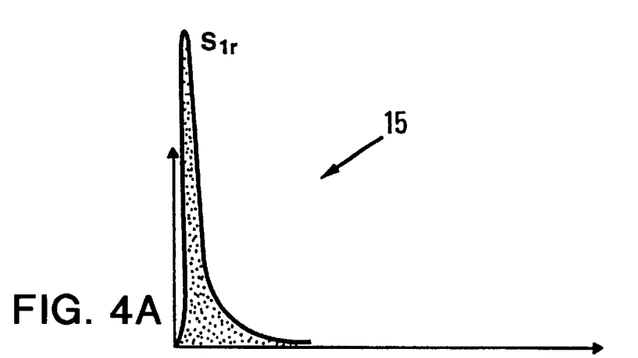
FIG. 4 illustrates an application example.
Figure 4B:
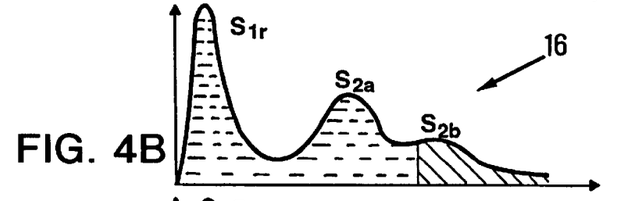
Figure 4C:
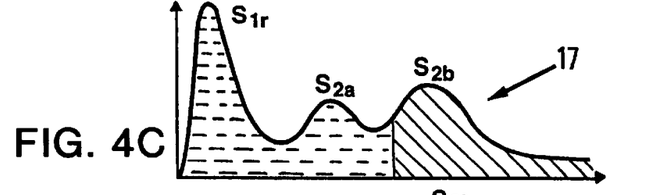
Figure 4D:
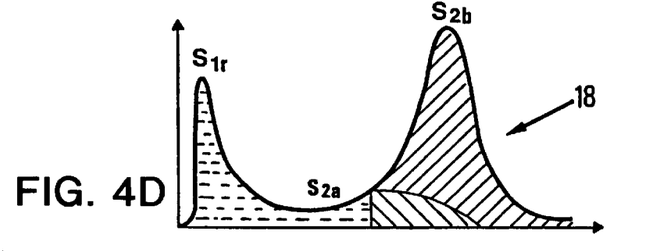
Figure 4E:
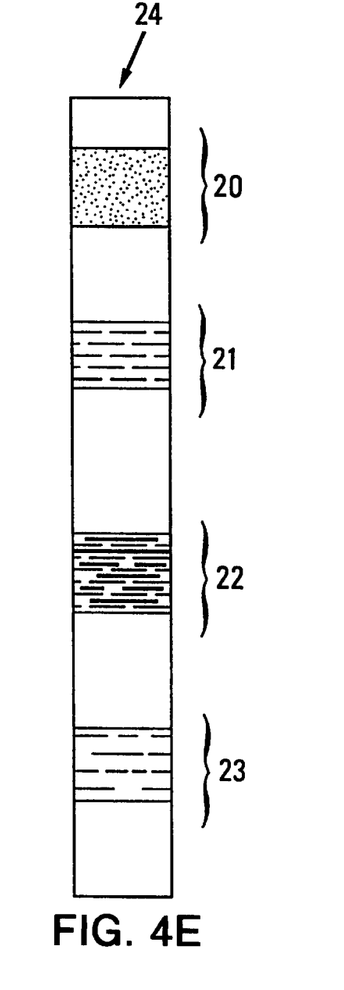

FIG. 3 shows an illustration of the magnitudes representative of the hydrocarbon-containing compounds contained in an impregnated reservoir rock according to the composition shown in FIG. 1.

It can be seen that, under the heating conditions described in FIG. 2, an impregnated rock containing heavy products (resins, asphaltenes and/or kerogens) produces, during pyrolysis, a first peak $S_{1r}$, a peak $S_{2a}$ and a peak $S_{2b}$ bearing respectively reference numbers 10, 11 and 12.

Peaks $S_{1r}$ and $S_{2a}$ (10, 11) correspond to the thermovaporization of the hydrocarbons below about $C_{40}$ present in the reservoir sample, whereas peak $S_{2b}$ (12) corresponds to the hydrocarbon-containing compounds resulting from the cracking by pyrolysis of the resins and the asphaltenes and/or the kerogen that constitute the heavy compounds.

Of course, for an impregnated reservoir rock that contains no resins and asphaltenes (NSO), the characterization will only comprise a peak $S_{1r}$ (10) and a peak $S_{2a}$ (11).

In the case of an impregnated rock that contains quantities of NSO, a peak $S_{2b}$ whose amplitude will depend on said quantities appears.

Computing means determine the respective quantities of the different types of hydrocarbons (light hydrocarbons, heavy hydrocarbons, the total amount of resins and asphaltenes and/or kerogen) as a function of the shape, of the amplitude of said peaks and of the organic carbon remaining after the pyrolysis.

In fact, the pyrolysis of the heavy products, notably the asphaltenes, always goes together with the formation of coke. The coke is thereafter burned in the second oxidation furnace of the ROCK-EVAL equipment and the $CO_2$ produced is measured by a peak representative of a characteristic magnitude $S_4$ (13). The percentage of residual organic carbon in the sample, called residual organic carbon $R_C$ remaining after pyrolysis, is thus determined.

Elemental analyses performed on the coke show that its organic carbon content is 90% on average.

The total quantity Q of heavy products contained in the sample is determined for each pyrolyzed sample by adding to the quantity of compounds represented by peak $S_{2b}$, the quantity of hydrocarbon-containing compounds represented by the coke formed, the latter being obtained from the residual carbon $R_C$ determined by oxidation in the ROCK-EVAL device. The quantity Q is then equal to:

$$Q = S_{2b} + 10 R_C / 0.9$$

Q and $S_{2b}$ being expressed in milligrams per gram.

Q will be called NSO when the products are mainly resins and asphaltenes.

Q can be called KERO when the products are mainly kerogen.

The amount of the tars settled in the reservoir can be assessed from this quantity Q or NSO.

Insoluble organic matter fragments (for example carbonaceous fragments in gritty reservoirs) or mother rock intercalations are commonly present in reservoirs. Under such conditions, the insoluble organic matter of these fragments or of these mother rock intercalations can be mistaken, in pyrolysis, for the presence of tars. In fact, the compounds from the thermal cracking of the insoluble organic matter appear at the level of peak $S_{2b}$ with the formation of coke.

In order to differentiate kerogen from the tars, the values of a production index IP calculated according to the following formula are used:

$$IP = (S_{1r} + S_{2a}) / (S_{1r} + S_{2a} + S_{2b}).$$

A low IP value shows the presence of kerogen, $S_{2b}$ is then considered to represent the pyrolyzable part of the kerogen and not only those of the resins and asphaltenes. In this case, the calculated quantity Q represents the quantity of kerogen.

The present method has been controlled by solvent extraction of heavy compounds. It has thus been checked that the value of 0.4 for IP is a good cut-off for differentiating the kerogen from the heavy extractable compounds (resins and asphaltenes). This value can possibly be made more precise by means of a prior calibration of the samples studied.

FIG. 4 shows four examples of pyrolysis on rock samples containing different types of organic matter.

Reference number 24 shows a lithologic representation in which reference number 20 represents a reservoir formation containing gas, reference number 21 represents a reservoir rock containing liquid hydrocarbons, reference number 22 represents a reservoir rock containing resins and asphaltenes or tars, and reference number 23 represents a mother rock intercalation containing kerogen (insoluble organic matter).

Samples taken in each of the four zones have allowed to obtain graphs 15, 16, 17 and 18 representing the magnitudes associated with the different hydrocarbons, according to the present invention.

Graph 15 shows the presence of only a peak $S_{1r}$ representative of a very light hydrocarbon such as gas.

Graph 16 shows the presence of the peak $S_{1r}$ and of the peak $S_{2a}$ representative of a liquid hydrocarbon. Peak $S_{2b}$ may or may not appear according to the proportion of resins and asphaltenes that the present reservoir rock 21 can contain. The value of IP is higher than 0.4.

Graph 17 shows the presence of a peak $S_{2b}$ that is relatively large in relation to peaks $S_{1r}$ and $S_{2a}$. This representation allows to recognize, in the reservoir rock of type 21, an intercalation of a level of tars or resins and asphaltenes bearing reference number 22.

Graph 18 mainly corresponds to the presence of only two peaks $S_{1r}$ and $S_{2b}$. Peak $S_{2a}$, generally small, and the heavy compounds (resins and asphaltenes) are concealed in peak $S_{2b}$. Rock 23 is identified as a mother rock, peak $S_{2b}$ being representative of the hydrocarbons resulting from the cracking of the kerogen. The value of IP is generally less than 0.4.

Figure 5:
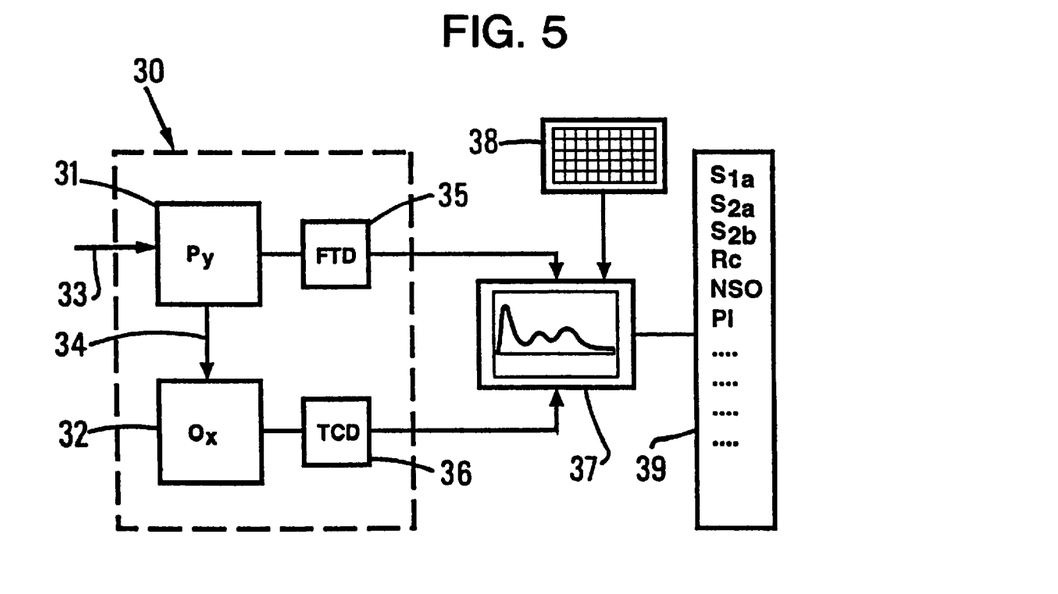
FIG. 5 shows a system for implementing the method.

FIG. 5 shows a schematization of the means for implementing the method according to the invention.

Reference number 30 represents the system comprising pyrolysis means 31, oxidation means 32, each respectively associated with hydrocarbon detection means 35 (for example a flame ionization detector FID) and with detection means 36 (for example a thermal conductivity detector TCD) for detecting the residual carbon oxidized in 32.

Arrow 33 symbolizes the means for feeding the sample into the system.

Reference number 37 shows the means intended for computing, storing and displaying the magnitudes detected by said system. Means 37 can also possibly control certain working parameters of system 30.

A keyboard 38 allows commands to be fed into means 37.

Reference number 39 shows a list of the characteristic magnitudes which can be provided by computing means 37. A recording example of the different magnitudes is illustrated by FIG. 6.

Figure 6:
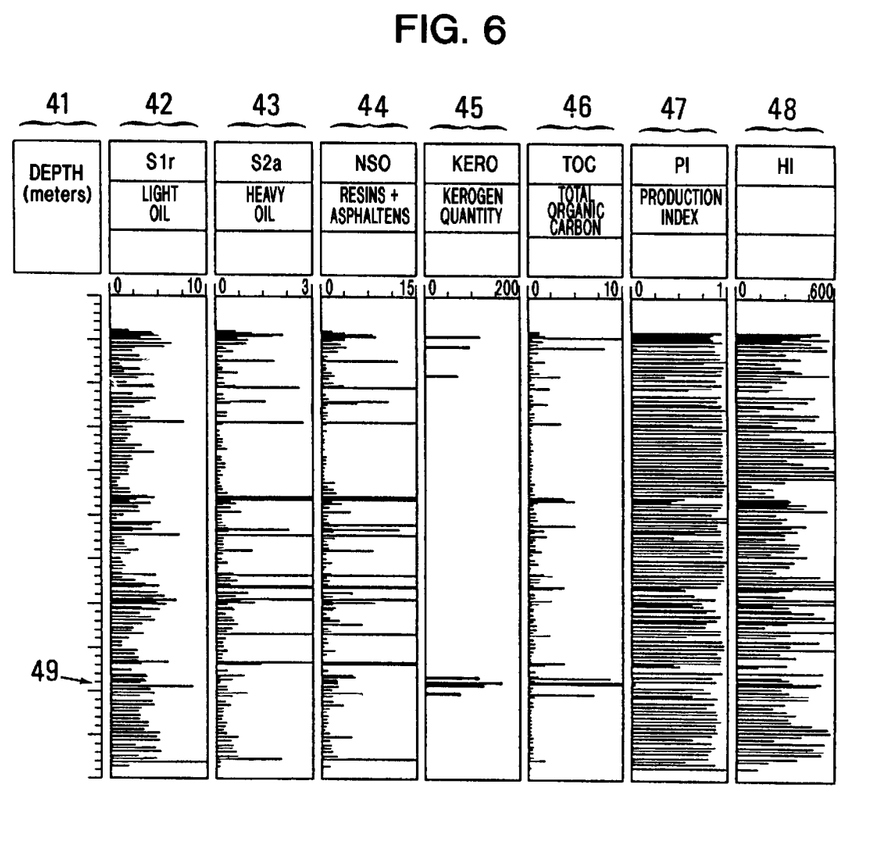
FIG. 6 illustrates an example of display of certain characteristic magnitudes.

FIG. 6 shows a representation of certain magnitudes characteristic of the rocks crossed by a hole between 1300 m and 2500 m. Column 41 represents the scale of depths in meters. Column 42 gives the quantity of light hydrocarbons, from peak $S_{1r}$, in milligrams per gram of sample. Column 43 gives the quantity of heavier hydrocarbons, from peak $S_{2a}$, in the same unit. Column 44 gives the quantity of NSO (resins and/or asphaltenes) obtained by means of peak $S_{2b}$ and of peak $S_4$. Column 45 shows and gives the quantity KERO of kerogen. Column 46 gives the total quantity of organic carbon contained in the sample, in percentage with respect to the weight of sample. Column 47 gives the value of the production index calculated from peaks $S_{1r}$, $S_{2a}$ and $S_{2b}$. According to a given cut-off value, for example 0.4, the calculated proportion of NSO is identified as true kerogen (column 5) or NSO (column 44). It can be noticed that the samples at the depth referenced 49 have low production indices, of the order of 0.1, and that the presence of kerogen is indicated. It can be deduced that, at this level, the sediments contain mother rock intercalations. Column 48 gives a hydrogen number.

With the method according to the invention, it is also advantageous to use the magnitudes $S_{1r}$, $S_{2a}$, $S_{2b}$ and $R_C$ obtained on rock samples crossed by a hole for assessing the API degree of the hydrocarbons contained in the reservoir rocks. Knowledge of the API degree is very interesting since the API degree is the magnitude that is commonly used for determining notably the mobility of hydrocarbons. It is well-known that liquid hydrocarbons having a API degree lower than 14 cannot be produced with conventional methods. Therefore, in some reservoirs, knowledge of the API degree acquired as the reservoir is being drilled allows to perform the production tests at the levels where production will be effective.

Furthermore, the method can be applied for determining the API degree of a produced petroleum without requiring the conventional laboratory measurements for measuring the API degree to be performed.

In order to determine the API degree, one or several laws or functions relating the API degree to at least one of the characteristic magnitudes $S_{1r}$, $S_{2a}$, $S_{2b}$ and possibly $Q=S_{2b}+10R_C/0.9$ must first be determined. To that effect, a certain number of samples of reservoir rocks and of petroleum that was contained in these reservoir rocks are collected. The API degree of the petroleum is measured by means of conventional laboratory methods on the one hand, and the corresponding sample is pyrolyzed according to the present method on the other hand.

It has been observed by the claimant that a magnitude D equal to one of the formulas as follows:

$$D = S_{2b}/(S_{1r} + S_{2a})$$

$$D = S_{1r}/(S_{1r} + S_{2a} + Q)$$

$$D = (S_{1r} + S_{2a})/(S_{1r} + S_{2a} + Q)$$

can be related to the API degree by a function $f$, for example of the form:

$$S_{1r}/(S_{1r} + S_{2a} + Q) = f(x) = a \times 10^{b \times e^{-ax}} + c$$

$$S_{2b}/(S_{1r} + S_{2a}) = f(x) = d - h \times \log x$$

$$S_{2b}/(S_{1r} + S_{2a}) = f(x) = g - h \times e^{-ax} + j^{-\beta x^2}$$

x being the API degree; a ranges between 0.11 and 0.12 and is preferably equal to 0.11482; b ranges between 1.7 and 2 and is preferably equal to 1.83; c is close to zero; d ranges between 2.1 and 2.3 and is preferably equal to 2.2273; h ranges between 1.3 and 1.4 and is preferably equal to 1.341; g ranges between 1.4 and 1.5 and is preferably equal to 1.4386; h ranges between 5.6 and 5.8 and is preferably equal to 5.7721; j ranges between 5.8 and 5.9 and is preferably equal to 5.8571; $\alpha$ is close to 2 and $\beta$ is close to 4.

The approximate, function $f$ is obtained according to the known mathematical methods for determining a function from a certain number of points.

Figure 7:
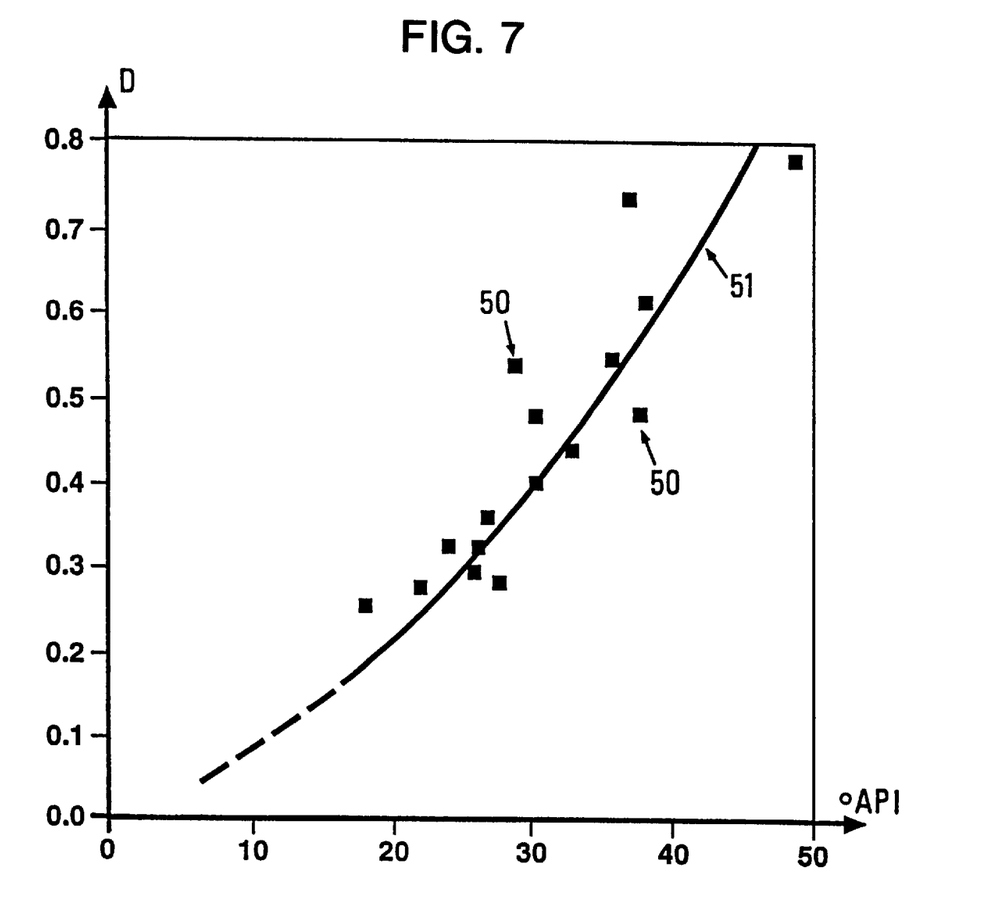
FIG. 7 illustrates a variant according to the invention.

FIG. 7 shows a set of points 50 placed on a graph where the API degree is shown as the abscissa and the magnitude $D=S_{1r}/(S_{1r}+S_{2a}+Q)$ as the ordinate.

The co-ordinates of points 50 have been obtained as described above, by measurements on petroleum and reservoir rock samples of different origins. In fact, the collection of the samples was not limited to a single oil field, and they have been gathered in different fields, at different depths and in various types of reservoirs.

Curve 51 representing function $f$ can therefore be used indiscriminately.

Once a function $f$ has been obtained, it can be easily stored, for example in the computing means 37 of FIG. 5. A computing program can determine D and, by applying function $f$, an approximate value of the API degree of the hydrocarbons that are or that were present in the sediments from which the rock sample was taken is obtained directly by computation.

In a variant, it will be possible to determine several functions relating the API degree to various magnitudes D calculated from $S_{1r}$, $S_{2a}$, $S_{2b}$ and $R_C$. It is possible to select, either manually or automatically, the function for obtaining the API degree, for example considering situations or circumstances that are already known.

Another variant of the method consists in determining a function $f1$, generally different but determined also according to $D=a \times 10^{b \times e^{-\alpha x}}+c$ from $f$, from samples of petroleum of different origins. For each petroleum sample, the API degree is measured according to the conventional laboratory methods and a small quantity of this sample is pyrolyzed according to the method of the present invention in order to calculate D according to one of the formulas given above. Once function $f1$ has been obtained, it will be used to determine the API degree of another petroleum, by determining for this one a value of D by pyrolyzing the petroleum sample according to the present method and by applying directly the function $f1$ obtained beforehand.

This variant thus replaces the conventional measurements of the API degree when the method according to the invention can be applied and when function $f$ or $f1$ has been determined. The present method is in some cases faster and easier than conventional methods.

In all the formulae, "e" is the natural log base which equals 2,718.

The entire disclosures of all applications, patents and publications, cited above, and of corresponding French Application FR-94/08.383, are hereby incorporated by reference.

We claim:

1. A method allowing the assessment of at least one petroleum characteristic of a sample coming from geologic sediments, said method comprising heating said sample in a nonoxidizing atmosphere according to several temperature rise stages, as follows:
   a) raising a temperature of said sample to a first temperature value of 180° to 200° C. for a first predetermined period of time,
   b) raising the temperature of the sample from the first temperature value to a second temperature value according to a first temperature gradient of 1° to 12° C./minute for a second predetermined period of time,
   c) raising the temperature of the sample from the second temperature value to a third temperature value of not more than 800° C. for a third predetermined period of time,
   d) determining in (a) magnitude $S_{1r}$ representative of quantities of light hydrocarbons of a carbon number less than about 15, determining in (b) magnitude $S_{2a}$, representative of quantities of medium hydrocarbons of a carbon number between 15 and 40, and determining in (c) magnitude $S_{2b}$, representative of quantities of heavy hydrocarbon-containing compounds of a carbon atom number greater than about 40, and
   e) using said magnitudes to determine at least one petroleum characteristic of said sample, said characteristic comprising a quantity Q representative of asphaltenes, resins and kerogen in said sample, production index IP, API degree, magnitude D, or a function $f$ of said characteristic.

2. The method as claimed in claim 1, further comprising burning any residue of said sample formed in (a)–(b) at said third temperature value, and measuring a value $R_C$ representative of a quantity of residual organic carbon contained in said sample after pyrolysis.

3. The method as claimed in claim 2, wherein the quantity Q is calculated according to the formula as follows:

$$Q=S_{2b}+10R_C/0.9$$

4. The method as claimed in claim 1, further comprising calculating the production index IP according to the formula as follows:

$$IP=(S_{1r}+S_{2a})/(S_{1r}+S_{2a}+S_{2b})$$

wherein if IP>$\mu$, the sample contains resins, asphaltenes or both and, if IP>$\mu$, the sample contains kerogen, wherein $\mu$ is a value of 0 to 1.

5. The method according to claim 1, wherein the second temperature value is not more than 370° C.

6. The method according to claim 1, wherein in (c) the temperature of the sample is raised from said second temperature value to said third temperature value according to a second temperature gradient greater than 12° C./minute.

7. The method as claimed in claim 3, wherein said sample is a piece of a reservoir rock, said method further comprising:

calculating a magnitude D for several first reservoir rock samples from at least one of the magnitudes $S_{1r}$, $S_{2a}$, $S_{2b}$ and Q, measuring an API degree of petroleum produced by said first reservoir rock samples, determining an approximate value of function $f$ relating the measured API degree to said magnitude D of said first reservoir rock samples, and determining an approximate value of an API degree of petroleum present in a second reservoir rock by taking at least one sample of said second reservoir rock and calculating the corresponding magnitude D of said second reservoir rock and using said approximate value of function $f$ to calculate the API degree of said second reservoir rock.

8. The method as claimed in claim 3, wherein said sample is petroleum produced from a first reservoir, said method further comprising:

calculating a magnitude D for several samples coming from different reservoirs, from at least one of the magnitudes $S_{1r}$, $S_{2a}$, $S_{2b}$ and Q, measuring an API degree of said samples, determining an approximate value of function $f1$ relating the measured API degree to magnitude D of said samples, and determining an approximate value of an API degree of a petroleum sample produced from a second reservoir by calculating the magnitude D corresponding to the petroleum sample from said second reservoir and using said approximate value of function $f1$ to calculate the API degree of the petroleum sample from said second reservoir.

9. The method as claimed in claim 3, wherein the magnitude D is calculated from at least one of the following formulas:

$$D = S_{2b}/(S_{1r} + S_{2a}),$$

$$D = S_{1r}/(S_{1r} + S_{2a} + Q),$$

$$D = (S_{1r} + S_{2a})/(S_{1r} + S_{2a} + Q).$$

10. The method as claimed in claim 4, wherein $\mu$ is about 0.4.

11. The method as claimed in claim 7, wherein the function $f$ has the form as follows:

$$D=a(10^{b(e-\alpha x)})+C$$

x being the API degree; a ranges between 0.11 and 0.12; b ranges between 1.7 and 2; c is about zero and $\alpha$ is about 2.

12. The method as claimed in claim 8, wherein the function $f1$ or $f$ has the form as follows:

$$D=a(10^{b(e-\alpha x)})+C$$

x being the API degree; a ranges between 0.11 and 0.12; b ranges between 1.7 and 2; C is about zero and $\alpha$ is about 2.

13. The method according to claim 11, wherein a is 0.11482.

14. The method according to claim 11, wherein b is 1.83.

15. The method according to claim 12, wherein a is 0.11482.

16. The method according to claim 12, wherein b is 1.83.

17. A method of determining an API degree of a sample coming from geologic sediments, said method comprising heating several first samples in a nonoxidizing atmosphere according to several temperature rise stages, as follows:

a) raising a temperature of each sample to a first temperature value of 180° to 200° C. for a first predetermined period of time, b) raising the temperature of the sample from the first temperature value to a second temperature value according to a temperature gradient of 1° to 12° C./minute for a second predetermined period of time, c) raising the temperature of the sample from the second temperature value to a third temperature value of not more than 800° C. for a third predetermined period of time, d) determining respectively in (a), (b) and (c) magnitudes $S_{1r}$, $S_{2a}$ and $S_{2b}$ representative of a quantity of hydrocarbon-containing compounds contained in said sample and Q, and e) calculating a magnitude D for several first samples from at least one of the magnitudes $S_{1r}$, $S_{2a}$, $S_{2b}$ and Q, f) measuring an API degree of petroleum produced by said first samples, g) determining an approximate function $f$ relating the measured API degree to magnitude D in the first samples, and h) determining an approximate value of an API degree of petroleum present in a second sample by calculating the corresponding magnitude D of said second sample and using said function $f$ to calculate the API degree of said second sample.

18. The method as claimed in claim 17, wherein the magnitude D of said several first samples and said second sample is calculated from at least one of the following formulas:

$$D = S_{2b}/(S_{1r} + S_{2a}),$$

-continued $$D = S_{1r}/(S_{1r} + S_{2a} + Q),$$

$$D = (S_{1r} + S_{2a})/(S_{1r} + S_{2a} + Q).$$

19. The method as claimed in claim 17, wherein the function $f$ has the relationship:

$$D = a(10^{b(e-\alpha x)}) + C$$

x being the API degree; a ranges between 0.11 and 0.12; b ranges between 1.7 and 2; c is about zero and $\alpha$ is about 2.

* * * * *